US012582375B2

(12) United States Patent
Bedingham et al.

(10) Patent No.: US 12,582,375 B2
(45) Date of Patent: Mar. 24, 2026

(54) MODULAR AUSCULTATION DEVICE

(71) Applicant: Solventum Intellectual Properties Company, Maplewood, MN (US)

(72) Inventors: William Bedingham, Woodbury, MN (US); J. Peter Robinson, St. Helens (GB)

(73) Assignee: Solventum Intellectual Properties Company, Maplewood, MN (US)

( * ) Notice: Subject to any disclaimer, the term of this patent is extended or adjusted under 35 U.S.C. 154(b) by 220 days.

(21) Appl. No.: 18/253,825

(22) PCT Filed: Dec. 1, 2021

(86) PCT No.: PCT/IB2021/061194
§ 371 (c)(1),
(2) Date: May 22, 2023

(87) PCT Pub. No.: WO2022/123399
PCT Pub. Date: Jun. 16, 2022

(65) Prior Publication Data
US 2024/0008835 A1 Jan. 11, 2024

Related U.S. Application Data

(60) Provisional application No. 63/199,178, filed on Dec. 11, 2020.

(51) Int. Cl.
*A61B 7/04* (2006.01)
(52) U.S. Cl.
CPC ..................................... *A61B 7/04* (2013.01)

(58) Field of Classification Search
CPC ....................................................... A61B 7/04
See application file for complete search history.

(56) References Cited

U.S. PATENT DOCUMENTS

| | | | | |
|---|---|---|---|---|
| 4,064,965 A | * | 12/1977 | Brown | A61B 7/02 |
| | | | | 181/135 |
| 4,071,694 A | | 1/1978 | Pfeiffer | |
| 4,200,169 A | | 4/1980 | MacDonald, III et al. | |
| 4,770,270 A | | 9/1988 | Grimm | |
| 5,104,158 A | * | 4/1992 | Meyer | F16L 37/0841 |
| | | | | 285/308 |

(Continued)

FOREIGN PATENT DOCUMENTS

| | | |
|---|---|---|
| CN | 2673304 Y | 1/2005 |
| CN | 210408454 U | 4/2020 |

(Continued)

OTHER PUBLICATIONS

International Search Report for PCT International Application No. PCT/IB2021/061194, mailed on Feb. 18, 2022, 3 pages.

*Primary Examiner* — Andrew Sniezek

(57) ABSTRACT
An auscultation device having a headset, a chest piece, and tubing connecting the chest piece to the headset. At least one connector disposed in the tubing between the headset and the chest piece and the at least one connector comprising a first female connector portion and a second male connector portion. The first female connector portion having a receiving cavity and a collar which is slidable and used to lock the first and second portions together, and the second male connector portion having a through hole, a compressible O-ring, and a latching ring collar.

16 Claims, 14 Drawing Sheets

(56)                    References Cited

U.S. PATENT DOCUMENTS

| | | | |
|---|---|---|---|
| 5,347,583 | A | 9/1994 | Dieken et al. |
| 5,650,598 | A * | 7/1997 | Abelson .................. A61B 7/02 |
| | | | 181/131 |
| 5,717,769 | A * | 2/1998 | Williams ................ A61B 7/04 |
| | | | 381/67 |
| 5,932,849 | A | 8/1999 | Dieken |
| 5,945,640 | A | 8/1999 | Rossini et al. |
| 8,396,228 | B2 * | 3/2013 | Bilan ...................... A61B 7/04 |
| | | | 381/67 |
| 9,973,847 | B2 | 5/2018 | Wong |
| D820,981 | S | 6/2018 | Johnson |
| 2019/0274656 | A1 | 9/2019 | Pande et al. |

FOREIGN PATENT DOCUMENTS

| | | |
|---|---|---|
| CN | 211460270 U | 9/2020 |
| WO | 2003075710 | 9/2003 |

* cited by examiner

14

30

12

34

36

10

32

MODULAR AUSCULTATION DEVICE

CROSS REFERENCE TO RELATED APPLICATIONS

This application is a national stage filing under 35 U.S.C. 371 of PCT/IB2021/061194, filed Dec. 1, 2021, which claims the benefit of U.S. Application No. 63/199,178, filed Dec. 11, 2020, the disclosure of which is incorporated by reference in its/their entirety herein.

FIELD

The present disclosure generally relates to auscultation and, more particularly, to auscultation devices with modularity.

SUMMARY

Conventional stethoscopes are designed for and constructed with a particular sound sensor—by way of example, mechanical, disposable, or digital. The embodiments of the present disclosure enable a user to purchase one type of stethoscope, by way of example, a personal, high-quality headset, that can be coupled to a variety of sound sensors—mechanical, disposable, digital or electronic, and the like. With these devices, a user could purchase a mechanical sound sensor, digital sensor, or combinations thereof, as well as replacement and/or backup sound sensors, and replace them easily and without wearing out or affecting the flexible tubing on the device.

Additionally, disposable stethoscopes used with infectious patients and isolation rooms can sometimes be constructed of lower quality materials and have inferior sound quality, fit, and noise isolation when compared to a user's personal headset—but yet can be functional and serve an important purpose where use of a personal, non-disposable stethoscope might not be recommended. If the user is wearing personal protective equipment (hood, gown, mask, googles, face shield, gloves) it can be difficult to attach and use a "patient room scope" without compromising safety. The embodiments of the present disclosure enable a user's personal headset to be positioned under the personal protective equipment (PPE) and be readily attached to a disposable (or semi disposable) sound sensor and/or a sound sensor on an extra-long portion of flexible tubing. After use, the disposable sound sensor assembly can be ejected. The personal headset and interface can remain effectively clean and can be easily decontaminated.

DETAILED DESCRIPTION

Figure 1:
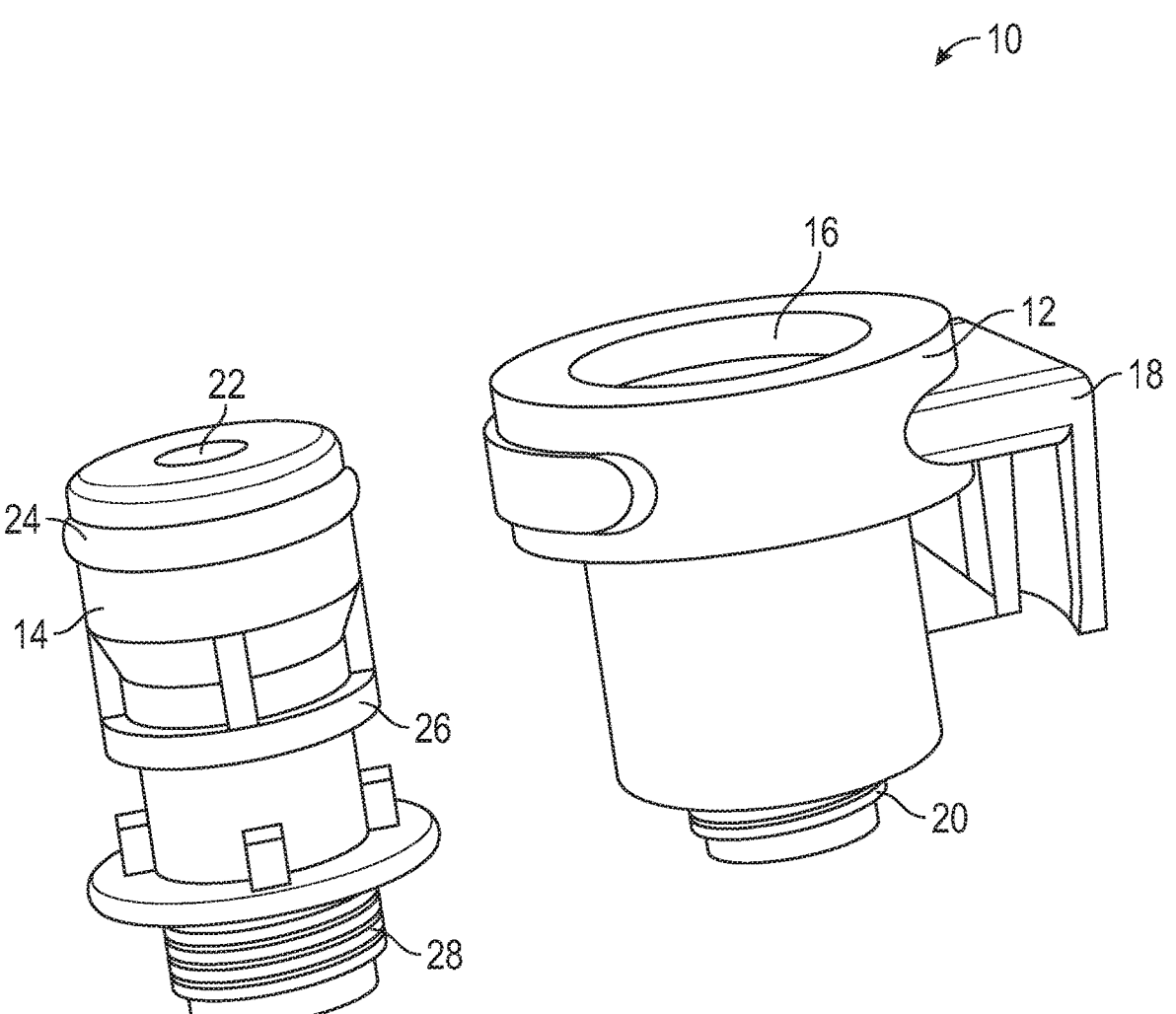
FIG. 1 is a perspective view of first and second portions of a connector according to an embodiment of the present disclosure.

Referring to FIG. 1, which is a perspective view of a connector 10 according to an embodiment of the present disclosure, the connector includes a first, female connector portion 12 and a second, male connector portion 14. First portion 12 includes a receiving cavity 16, a collar 18, which can be slidable and used as a feature to lock first and second portions together, and a threaded portion 20 that can be used to couple first portion with an electronic module. Second portion 14 includes a through hole or passage 22, a compressible O-ring 24, a latching ring collar 26, and a threaded portion 28 that can be used to couple second portion with an electronic module 30 (see FIG. 2). In other embodiments, first and second connector portions can alternatively include barbs rather than threaded portions. Such barbs can be used to couple first and second connector portions directly to tubing.

Figure 2:
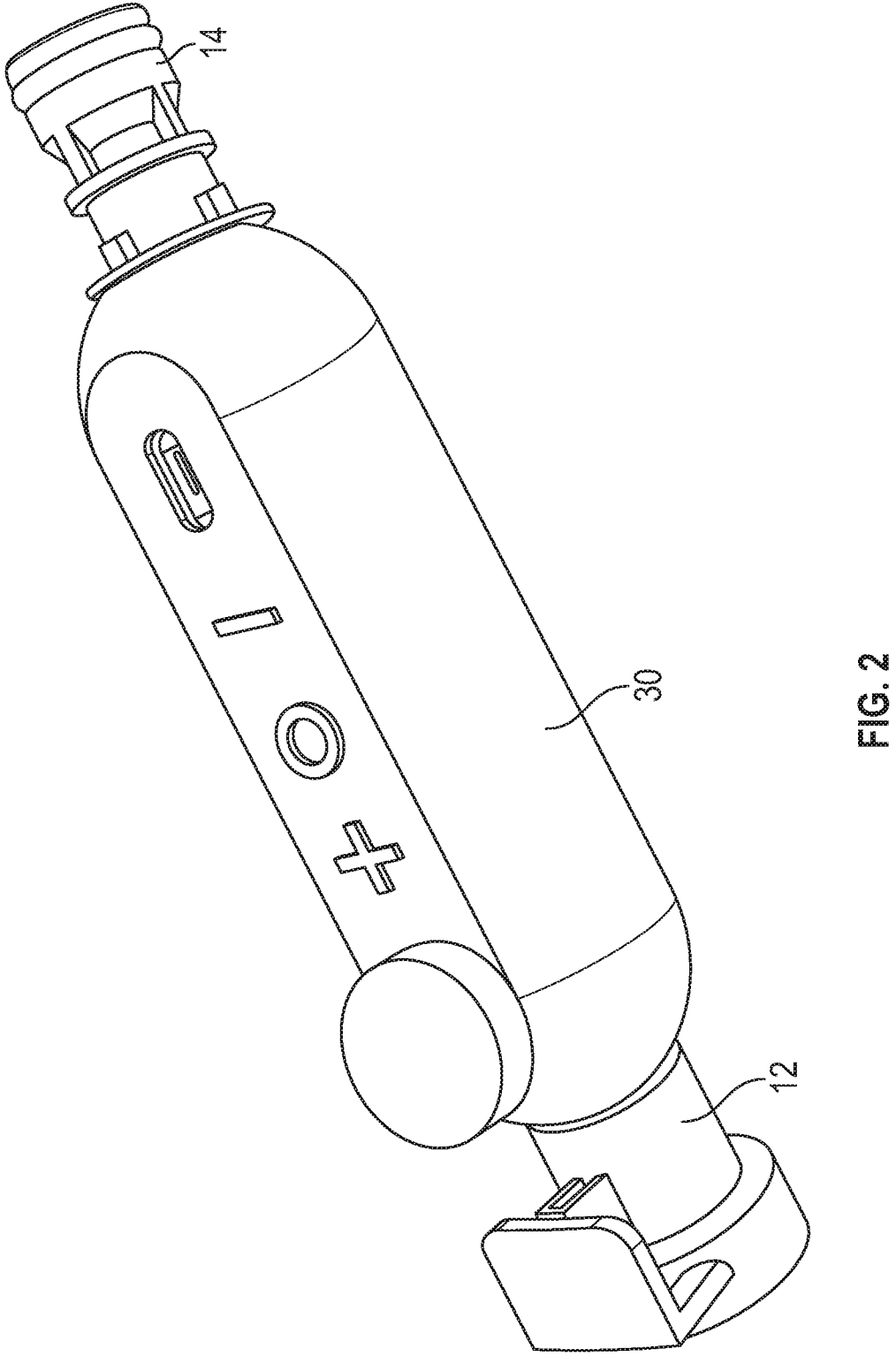
FIG. 2 is a perspective view of an electronic auscultation component with the first and second portions of the connector of FIG. 1 coupled thereto.
Figure 3:
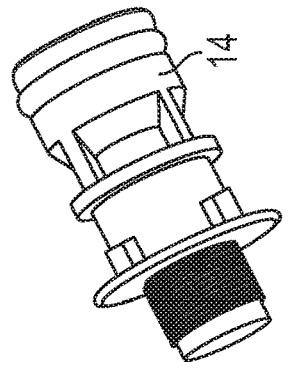
FIG. 3 is a perspective view of the electronic auscultation component with the first and second portions of the connector of FIG. 1 decoupled therefrom.
Figure 3:
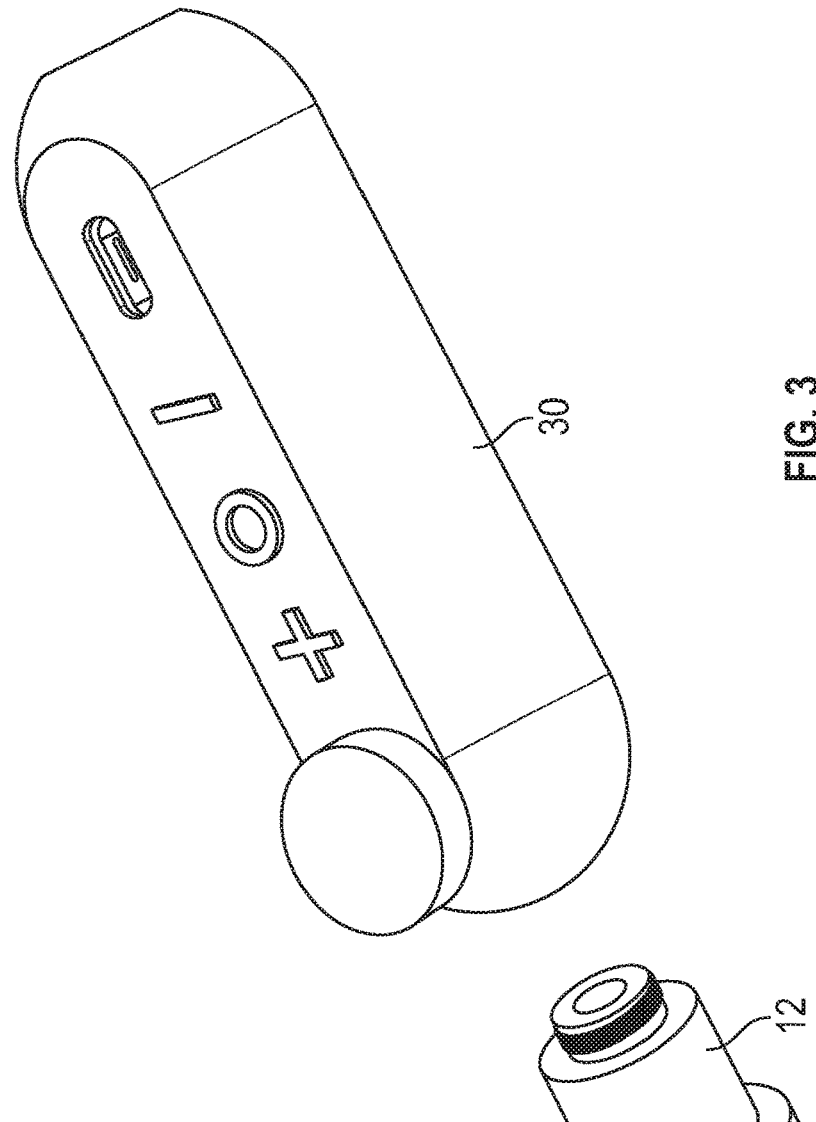
Figure 4:
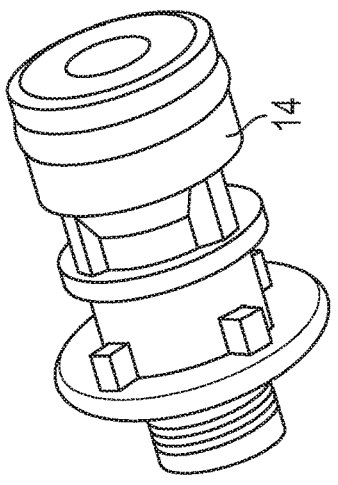
FIG. 4 is a perspective view of the electronic auscultation component with the first and second portions of the connector of FIG. 1 decoupled therefrom.
Figure 4:
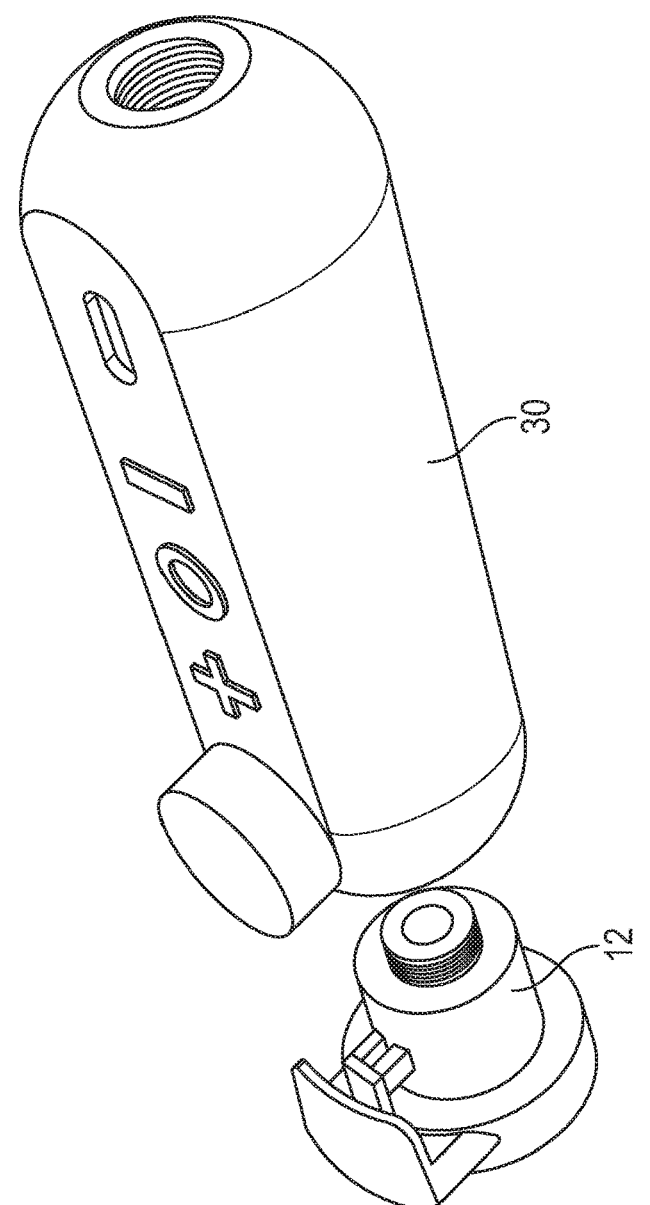
Figure 5:
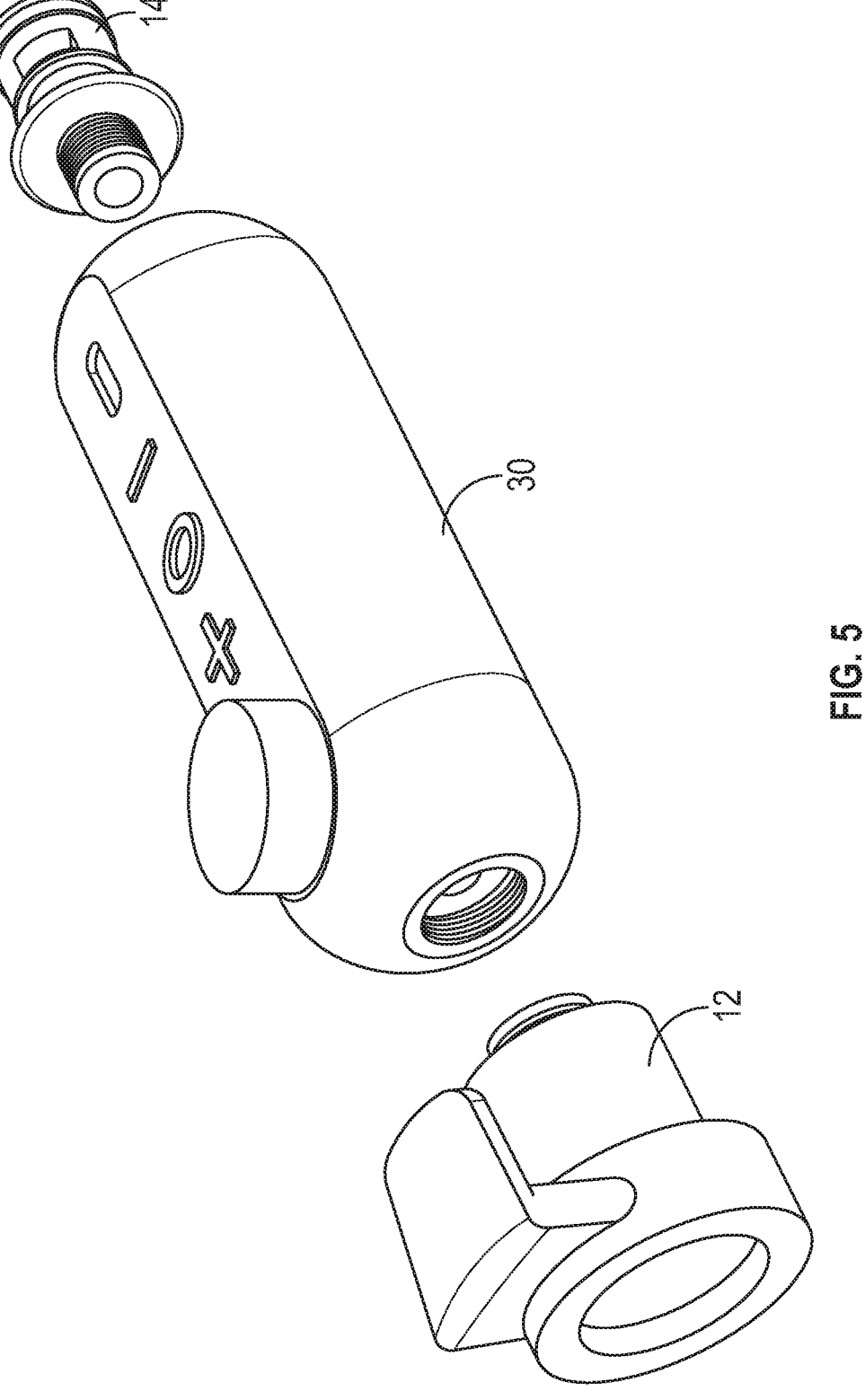
FIG. 5 is a perspective view of the electronic auscultation component with the first and second portions of the connector of FIG. 1 decoupled therefrom.

Referring to FIG. 2, which is a perspective view of an electronic or digital auscultation component with the first and second portions of the connector of FIG. 1 coupled thereto, first portion can be coupled to a first end of the electronic auscultation component and second portion can be coupled to a second end of the electronic auscultation component. To do this, referring to FIGS. 3-5, threaded portion of first portion can be used to couple first portion with a threaded portion of electronic module on the first end and threaded portion of second portion can be used to couple second portion with a threaded portion of electronic module on the second end.

Figure 6:
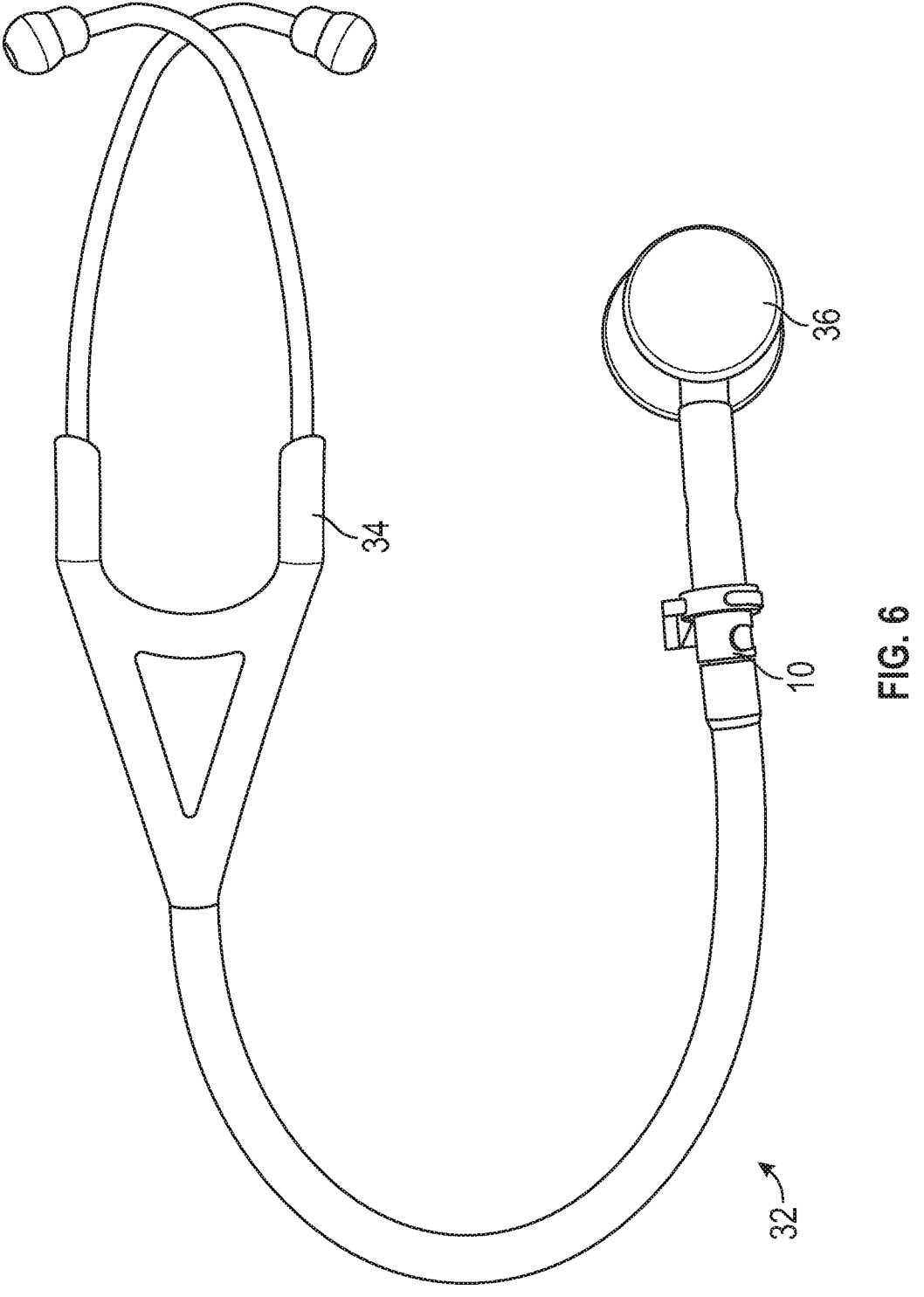
FIG. 6 is a top plan view of an auscultation device in a first configuration.

FIG. 6 depicts a top plan view of an auscultation device in a first configuration 32. In this configuration, auscultation device includes a modular connector at the distal end. More specifically, a headset section 34 is terminated with an open, first female pneumatic connector. In this embodiment, first, female connector has a barb fitting to interface with the headset tubing. First, female connector has a button feature that allows for the insertion/lock or unlock/removal/ejection of the distal chest piece section. Distal chest piece section has a male modular connector that inserts and locks into the female modular connector. Male connector has a barb fitting to interface with the chest piece tubing and the chest piece tubing connects to the chest piece 36 with a barb fitting. The device includes a mechanical sensor/chest piece. Examples of mechanical chest pieces are depicted and described in U.S. Pat. Nos. 4,200,169, 4,770,270, 5,945,640, and D820,981, the disclosures of which are incorporated by reference herein.

Figure 7:
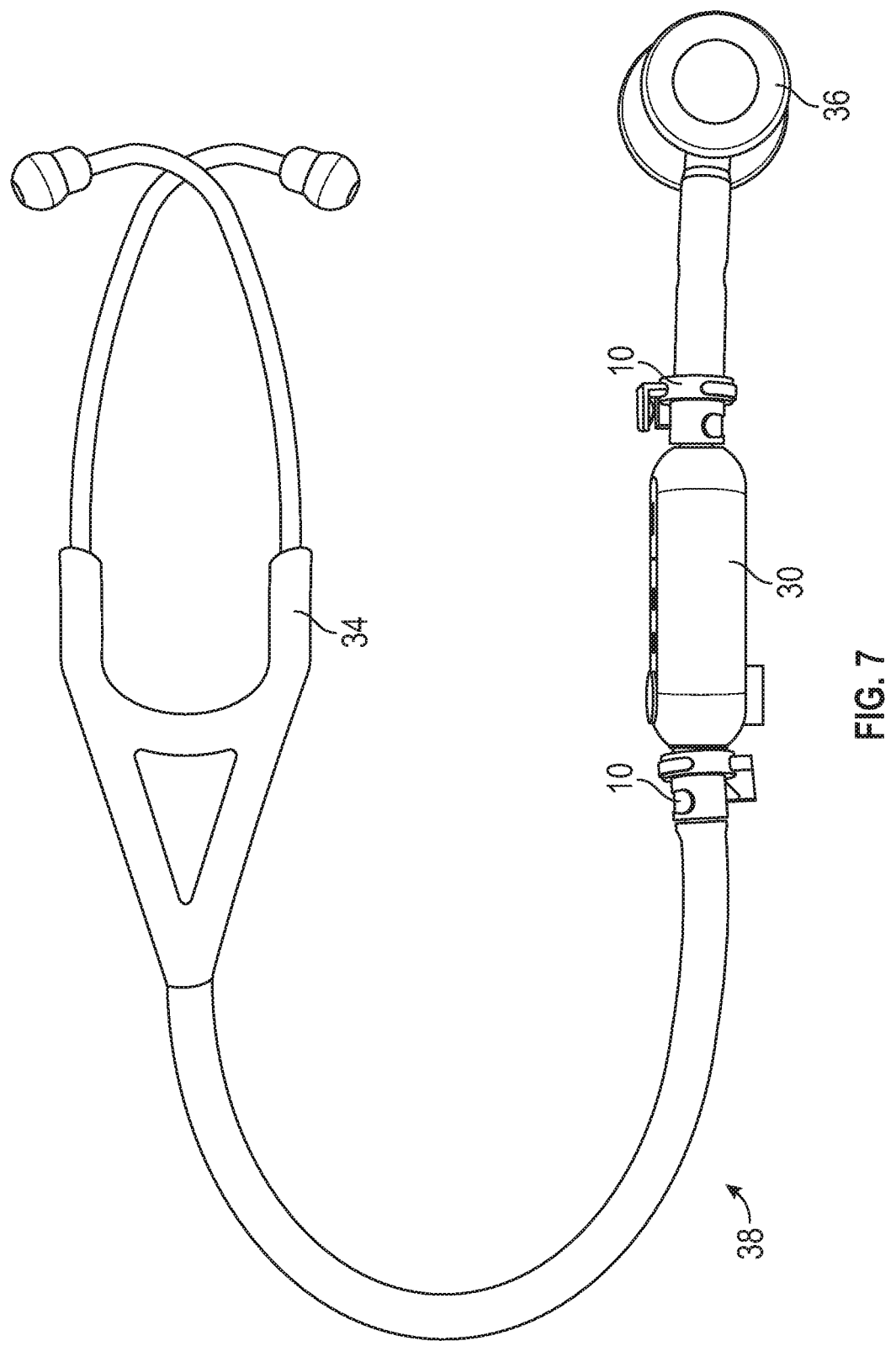
FIG. 7 is a top plan view of an auscultation device in a second configuration.

FIG. 7 depicts a top plan view of an auscultation device in a second configuration 38. In this configuration, auscultation device includes a modular connector at the distal end. More specifically, a headset section is terminated with an open, first female pneumatic connector. In this embodiment, first, female connector has a barb fitting to interface with the headset tubing. First, female connector has a button feature that allows for the insertion/lock or unlock/removal/ejection of the electronic module. The electronic module has a male modular connector threaded into the proximal section. The electronic module has a female modular connector threaded into the distal section. Distal chest piece section has a male modular connector that inserts and locks into the female modular connector. Male connector has a barb fitting to interface with the chest piece tubing. Chest piece tubing connects to the chest piece with a barb fitting. The device includes a mechanical sensor/chest piece. Examples of mechanical chest pieces are depicted and described in U.S. Pat. Nos. 4,200,169, 4,770,270, 5,945,640, and D820,981, the disclosures of which are incorporated by reference herein. The device includes an electronic module. Examples of electronic modules are depicted and described in U.S. Pat. No. 9,973,847, the disclosure of which is incorporated by reference herein.

Figure 8:
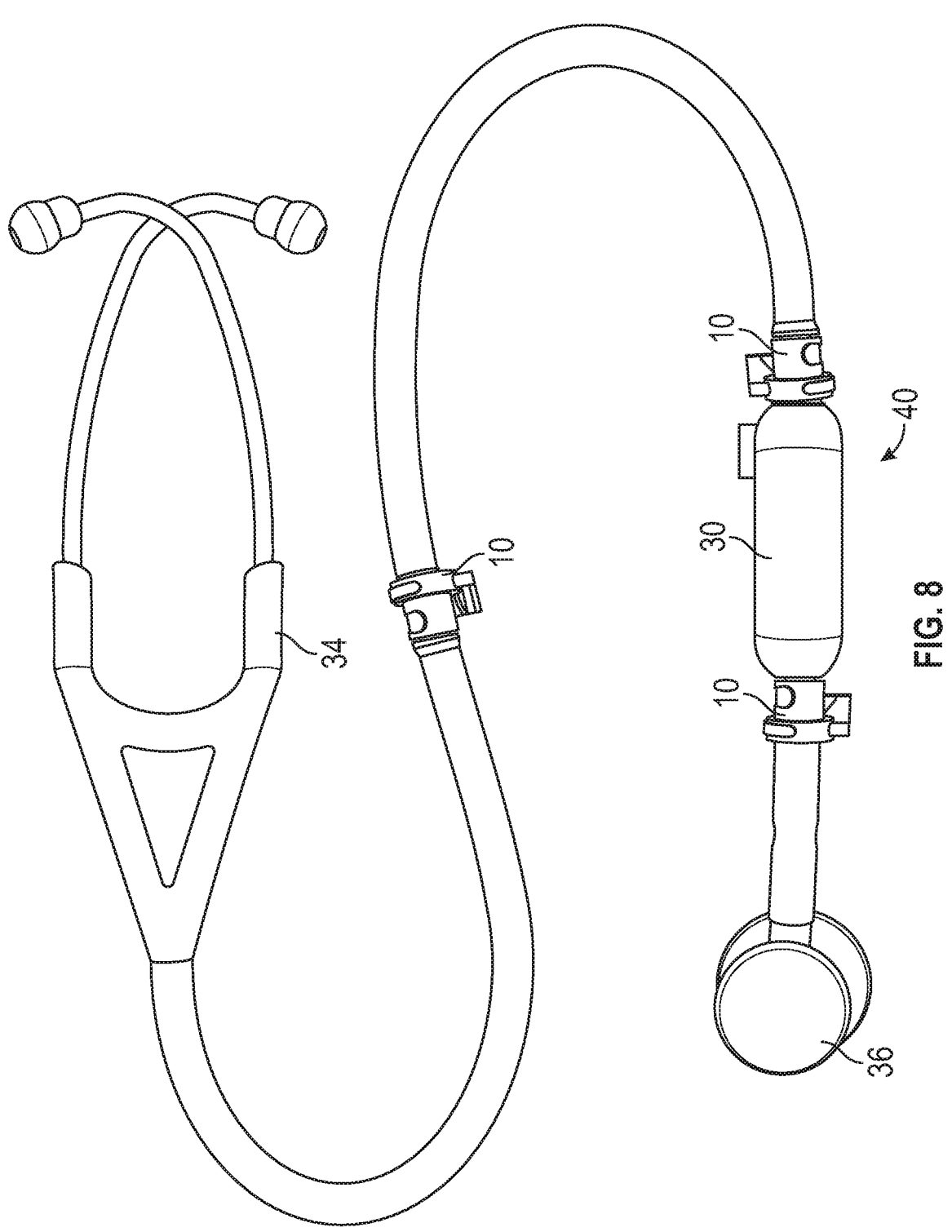
FIG. 8 is a top plan view of an auscultation device in a third configuration.

FIG. 8 depicts a top plan view of an auscultation device in a third configuration 40. In this configuration, auscultation device includes a modular connector at the distal end. More specifically, a headset section is terminated with an open, first female pneumatic connector. In this embodiment, first, female connector has a barb fitting to interface with the headset tubing. First, female connector has a button feature that allows for the insertion/lock or unlock/removal/ejection of a modular extension section. The extension section has a male modular connector at the proximal end and a bard connector to interface to the tubing. The extension section has a female modular connector at the distal end and a barb connector to interface with the tubing. The device includes a mechanical sensor/chest piece. Examples of mechanical chest pieces are depicted and described in U.S. Pat. Nos. 4,200,169, 4,770,270, 5,945,640, and D820,981, the disclosures of which are incorporated by reference herein. The device includes an electronic module. Examples of electronic modules are depicted and described in U.S. Pat. No. 9,973,847, the disclosure of which is incorporated by reference herein.

Figure 9:
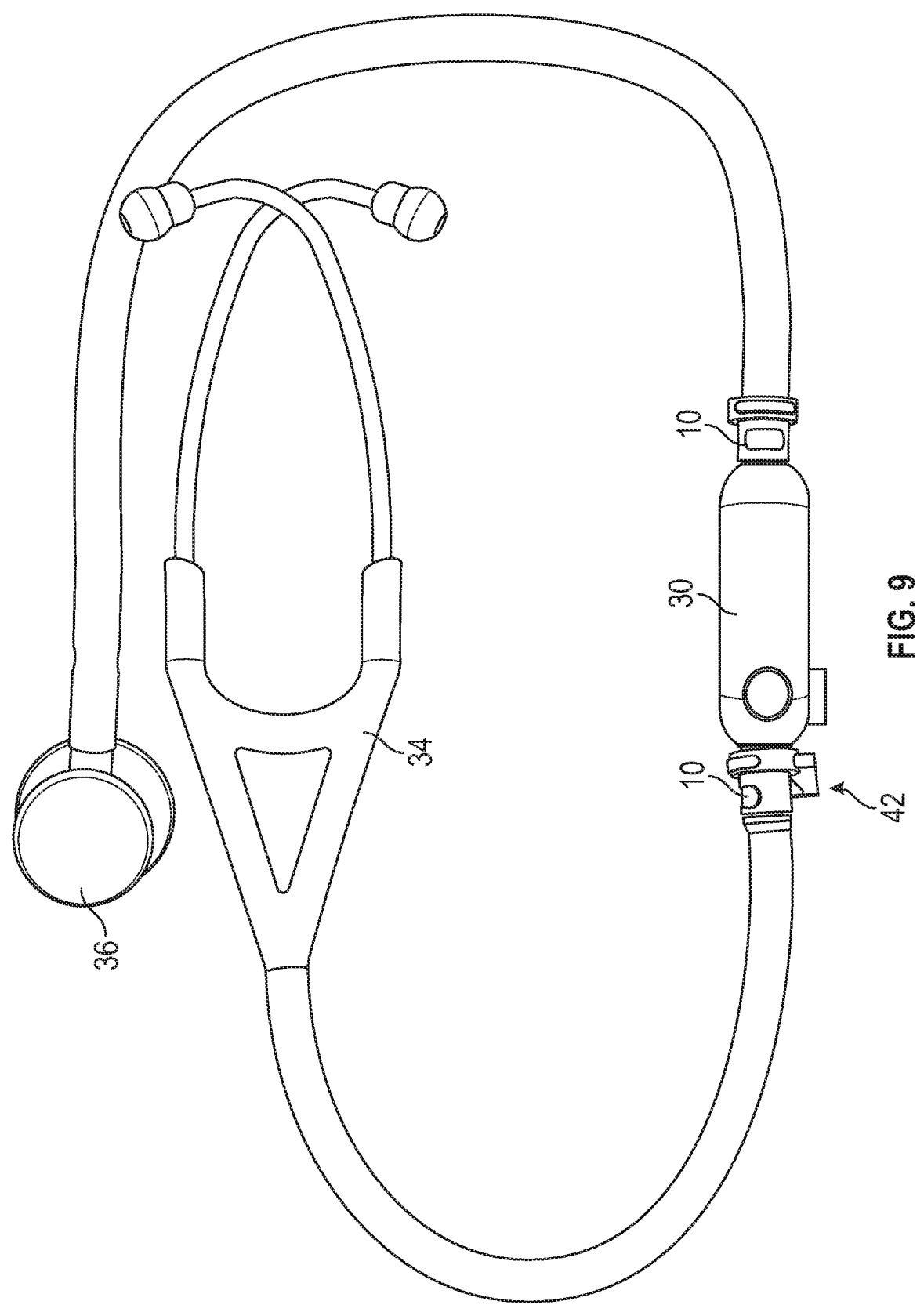
FIG. 9 is a top plan view of an auscultation device in a fourth configuration.

FIG. 9 depicts a top plan view of an auscultation device in a fourth configuration 42. In this configuration, auscultation device includes a modular connector at the distal end. More specifically, a headset section is terminated with an open, first female pneumatic connector. In this embodiment, first, female connector has a barb fitting to interface with the headset tubing. First, female connector has a button feature that allows for the insertion/lock or unlock/removal/ejection of a disposable modular chest piece section at the distal end. The disposable section has a male modular connector that interfaces with female modular connector of the electronic module. Male connector has a barb fitting to interface with the tubing of the disposable chest piece section. The device includes a mechanical sensor/chest piece. Examples of mechanical chest pieces are depicted and described in U.S. Pat. Nos. 4,200,169, 4,770,270, 5,945,640, and D820,981, the disclosures of which are incorporated by reference herein. The device includes an electronic module. Examples of electronic modules are depicted and described in U.S. Pat. No. 9,973,847, the disclosure of which is incorporated by reference herein.

Figure 10:
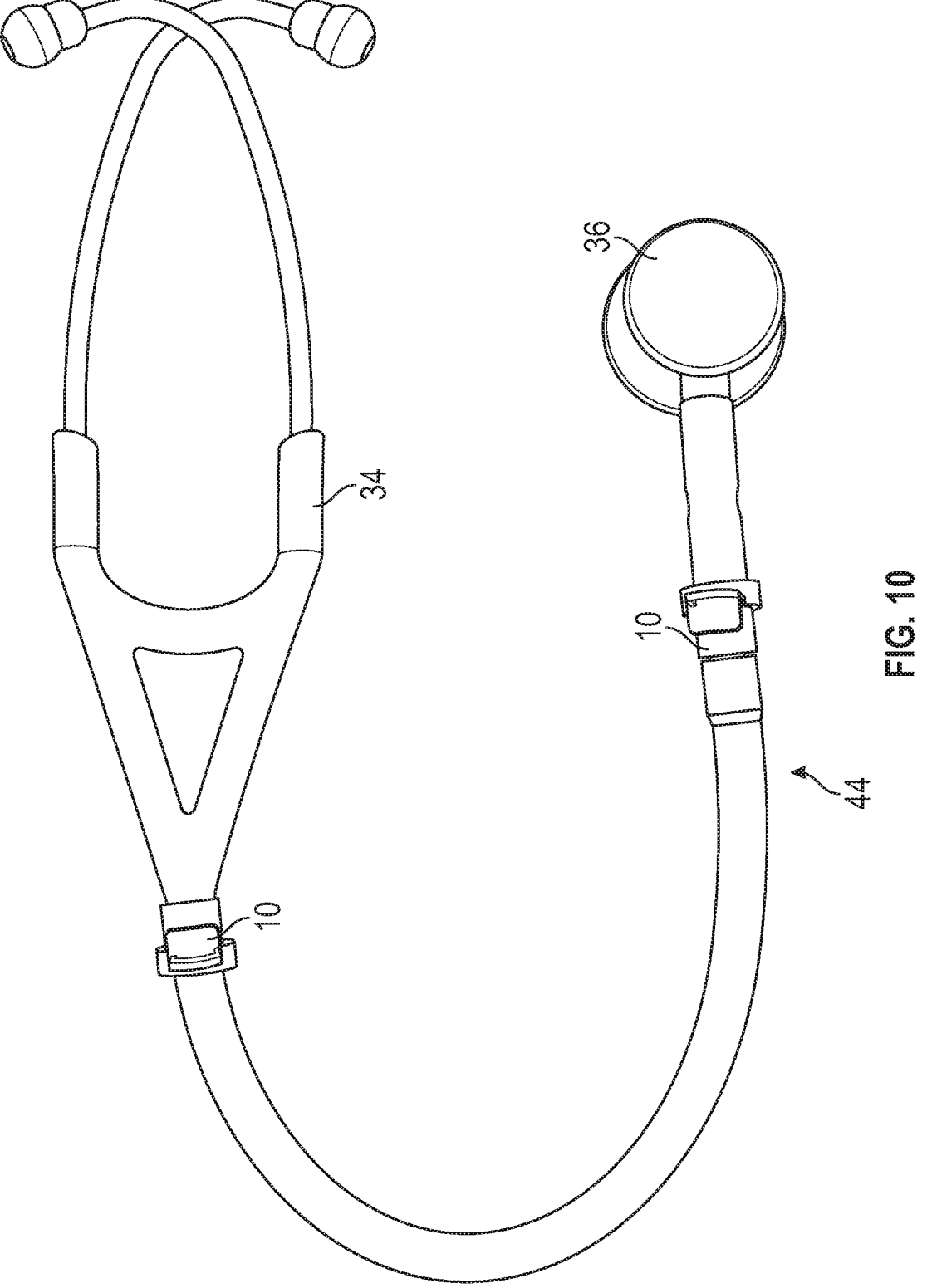
FIG. 10 is a top plan view of an auscultation device in a fifth configuration.

FIG. 10 depicts a top plan view of an auscultation device in a fifth configuration 44. In this configuration, auscultation device includes a modular connector at both the proximal and distal ends. More specifically, a headset section is terminated with an open, first female pneumatic connector at a proximal end. In this embodiment, first, female connector has a barb fitting to interface with the headset tubing. First, female connector has a button feature that allows for the insertion/lock or unlock/removal/ejection of a second portion of a modular connector. The second modular connector has a barb fitting to interface with a modular extension section tubing. The extension section has a female modular connector at the proximal end and a barb connector to interface to the tubing. Female connector has a button feature that allows for the insertion/lock or unlock/removal/ejection of the distal chest piece section. Distal chest piece section has a male modular connector that inserts and locks into the female modular connector. Male connector has a barb fitting to interface with the chest piece tubing and the chest piece tubing connects to the chest piece with a barb fitting. The device includes a mechanical sensor/chest piece. Examples of mechanical chest pieces are depicted and described in U.S. Pat. Nos. 4,200,169, 4,770,270, 5,945,640, and D820,981, the disclosures of which are incorporated by reference herein.

Figure 11:
FIG. 11 is a top plan view of an auscultation device in a sixth configuration.

FIG. 11 depicts a top plan view of an auscultation device in a sixth configuration 46 like that in FIG. 10. In this embodiment, an electronic chest piece 37 is included. The device includes digital sensor/chest piece. Examples of digital chest pieces are depicted and described in U.S. Pat. Nos. 4,071,694, 5,347,583, and 5,932,849, the disclosures of which are incorporated by reference herein.

Figure 12:
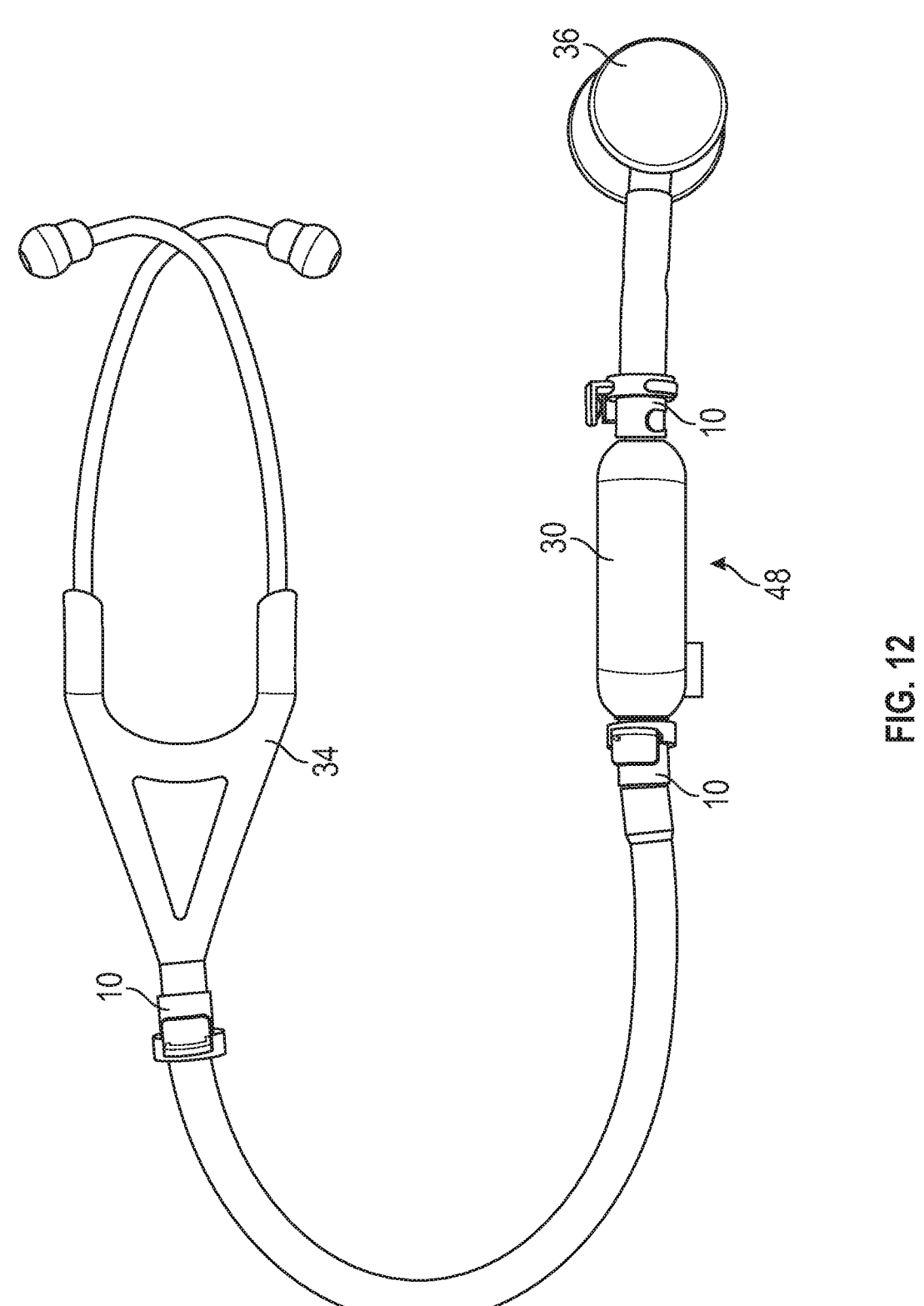
FIG. 12 is a top plan view of an auscultation device in a seventh configuration.

FIG. 12 depicts a top plan view of an auscultation device in a seventh configuration 48 like that in FIGS. 10 and 11. In this embodiment, an electronic auscultation component is included at a distal end thereof. The device includes a mechanical sensor/chest piece. Examples of mechanical chest pieces are depicted and described in U.S. Pat. Nos. 4,200,169, 4,770,270, 5,945,640, and D820,981, the disclosures of which are incorporated by reference herein. The device includes an electronic module. Examples of electronic modules are depicted and described in U.S. Pat. No. 9,973,847, the disclosure of which is incorporated by reference herein.

Figure 13:
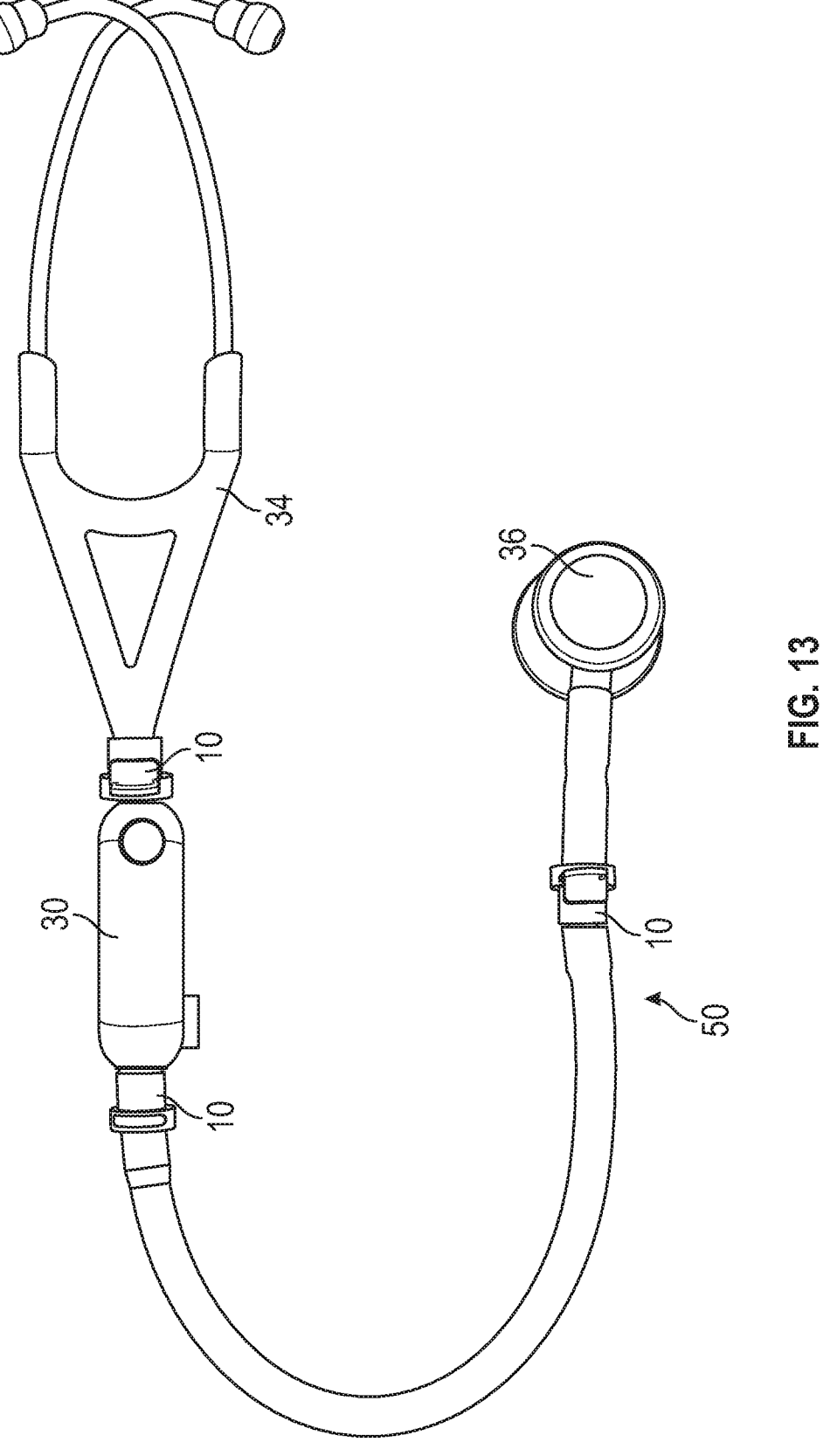
FIG. 13 is a top plan view of an auscultation device in an eighth configuration.

FIG. 13 depicts a top plan view of an auscultation device in a eighth configuration like that in FIGS. 10 and 11. In this embodiment, an electronic auscultation component is included at a proximal end thereof. The device includes a mechanical sensor/chest piece. Examples of mechanical chest pieces are depicted and described in U.S. Pat. Nos. 4,200,169, 4,770,270, 5,945,640, and D820,981, the disclosures of which are incorporated by reference herein. The device includes an electronic module. Examples of electronic modules are depicted and described in U.S. Pat. No. 9,973,847, the disclosure of which is incorporated by reference herein.

Figures 14A, 14B, 14C:
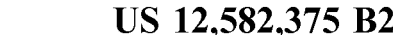
FIG. 14(a) depicts an auscultation device in a ninth configuration.
FIG. 14(b) depicts an auscultation device in a tenth configuration.
FIG. 14(c) depicts an auscultation device in an eleventh configuration.

Referring to FIG. 14(*a*), which depicts an auscultation device in a ninth configuration 52, a medical worker or user is outfitted with personal protective equipment (PPE). A stethoscope has a modular connector located at the proximal section near the headset and a mechanical chest piece with tubing and a modular connector is connected. The device includes a mechanical sensor/chest piece. Examples of mechanical chest pieces are depicted and described in U.S.

5

Pat. Nos. 4,200,169, 4,770,270, 5,945,640, and D820,981, the disclosures of which are incorporated by reference herein. The device includes an electronic module.

Referring to FIG. 14(*b*), which depicts an auscultation device in a tenth configuration 54, a medical worker or user is outfitted with personal protective equipment (PPE). A stethoscope has a modular connector located at the proximal section near the headset and an electronic chest piece with tubing and a modular connector is connected. In this embodiment, an electronic chest piece is included. Examples of digital chest pieces are depicted and described in U.S. Pat. Nos. 4,071,694, 5,347,583, and 5,932,849, the disclosures of which are incorporated by reference herein.

Referring to FIG. 14(*c*), which depicts an auscultation device in an eleventh configuration 56, a medical worker or user is outfitted with personal protective equipment (PPE). A stethoscope has a modular connector located at the proximal section near the headset and a disposable chest piece with tubing and a modular connector is connected.

The embodiments of the present disclosure enable a user to attach multiple end sound sensors (e.g., chest piece). The modular stethoscopes allow a user to easily attach a standard mechanical chest piece 36 or a digital chest piece 37. A health worker can quickly attach a disposable or semi disposable sound sensor. After the procedure, the health worker can dispose the distal sensor, secure it in the patient's room, or bag it for hospital reprocessing. The personal headset remains effectively clean. The personal headset can be worn under personal protective gear and easily accessed. This invention protects both the patient and the health worker from cross contamination.

The invention claimed is:

1. An auscultation device comprising:
a headset, a chest piece including a shaft, and tubing;
an accessory;
at least one connector including at least one of a first female connector portion and a second male connector portion;
the first female connector portion having a receiving cavity, a slidable collar, and a first threaded portion; and
the second male connector portion having a through hole, a compressible O-ring, a latching ring collar, and a second threaded portion,
wherein the at least one connector allows the auscultation device to be assembled into a plurality of assembled configurations, including:
a first assembled configuration that includes the at least one connector, the headset, the chest piece, and the tubing arranged in series, but omits the accessory, and which exhibits a first length from the headset to the chest piece; and
a second assembled configuration that includes the at least one connector, the headset, the chest piece, the tubing, and the accessory arranged in series, and which exhibits a second length from the headset to the chest piece greater than the first length.

2. The auscultation device of claim 1, wherein the accessory comprises an electronic auscultation component and the at least one connector comprises two connectors, and wherein, in the second assembled configured, the electronic auscultation component and the two connectors are disposed between the headset and the chest piece.

3. The auscultation device of claim 1, wherein the accessory comprises an electronic auscultation component and the at least one connector comprises three connectors, and wherein, in the second assembled configured, the electronic auscultation component and the three connectors are disposed between the headset and the chest piece.

4. The auscultation device of claim 1, wherein the chest piece is an electronic chest piece.

5. A kit, comprising:
a headset;
a chest piece including a shaft;
tubing;
at least one accessory; and
at least one connector,
wherein the at least one connector allows the headset, the chest piece, and the tubing to be assembled together into a plurality of assembled configurations, including:
a first assembled configuration that includes the at least one connector, the headset, the chest piece, and the tubing arranged in series, but omits the at least one accessory, and which exhibits a first length from the headset to the chest piece; and
a second assembled configuration that includes the at least one connector, the headset, the chest piece, the tubing, and the at least one accessory arranged in series, and which exhibits a second length from the headset to the chest piece greater than the first length.

6. The kit of claim 5, wherein the at least one accessory comprises an electronic module, wherein the at least one connector comprises a first connector and a second connector, and wherein, in the second assembled configuration:
the first connector is coupled to a first end of the electronic module and the chest piece; and
the second connector is coupled to a second end of the electronic module and the tubing.

7. The kit of claim 5, wherein the accessory comprises an electronic module, wherein the at least one connector comprises a first connector, a second connector, and a third connector, and wherein, in the second assembled configuration:
the first connector is coupled to a first end of the electronic module and the chest piece;
the second connector is coupled to a second end of the electronic module and a first end of the tubing; and
the third connector is coupled to a second end of the tubing and the headset.

8. The kit of claim 5, wherein the at least one connector comprises a first connector that includes a receiving cavity and a slidable collar.

9. The kit of claim 8, wherein the at least one accessory comprises an electronics module and the first connector further includes a threaded end to threadably couple to the electronics module.

10. The kit of claim 8, wherein the at least one connector further comprises a second connector that includes a through hole, a compressible O-ring, and a latching ring collar.

11. The kit of claim 10, wherein the at least one accessory comprises an electronics module, the first connector further includes a threaded end to threadably couple to a first end of the electronics module, and the second connector further includes a threaded end to threadably couple to a second end of the electronics module.

12. The kit of claim 5, wherein the chest piece comprises a first type of chest piece and the kit further includes a second type of chest piece different than the first type of chest piece.

13. The kit of claim 12, wherein the first type of chest piece comprises an electronic chest piece.

14. A kit, comprising:
a plurality of components that includes a headset, a chest piece including a shaft, and tubing;

at least one accessory; and first and second connectors, wherein the kit is assemblable into a plurality of assembled configurations, including:

a first assembled configuration that includes the first connector arranged in series with the plurality of components, but omits the at least one accessory and the second connector, and exhibits a first length from the headset to the chest piece; and a second assembled configuration that includes the first and second connectors arranged in series with the plurality of components and the at least one accessory and exhibits a second length from the headset to the chest piece greater than the first length.

15. The kit of claim 14, wherein the at least one accessory comprises an electronics component.

16. The kit of claim 15, wherein the tubing is first tubing and the at least one accessory comprises second tubing.

* * * * *